(12) United States Patent
Moorwood et al.

(10) Patent No.: US 8,916,532 B2
(45) Date of Patent: Dec. 23, 2014

(54) METHODS FOR ENHANCING UTROPHIN PRODUCTION VIA INHIBITION OF MICRORNA

(75) Inventors: Catherine Moorwood, Philadelphia, PA (US); Utpal Basu, Kolkata (IN); Gopal Patel, Roseville, CA (US); Olga Lozynska, Philadelphia, PA (US); Tejvir S. Khurana, Narnerth, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 822 days.

(21) Appl. No.: 12/989,758

(22) PCT Filed: Apr. 27, 2009

(86) PCT No.: PCT/US2009/041783
§ 371 (c)(1),
(2), (4) Date: Jan. 20, 2012

(87) PCT Pub. No.: WO2009/134710
PCT Pub. Date: Nov. 5, 2009

(65) Prior Publication Data
US 2012/0122953 A1    May 17, 2012

Related U.S. Application Data

(60) Provisional application No. 61/071,408, filed on Apr. 28, 2008.

(51) Int. Cl.
*A01N 43/04* (2006.01)
*C12N 15/00* (2006.01)
*C07H 21/04* (2006.01)

(52) U.S. Cl.
USPC ............... 514/44; 435/6; 435/91.1; 435/375; 536/23.1; 536/24.5

(58) Field of Classification Search
USPC ......... 435/91, 6, 91.1, 91.31, 455, 375, 45, 5; 514/44; 536/23.1, 24.5
See application file for complete search history.

(56) References Cited

U.S. PATENT DOCUMENTS

| | | | |
|---|---|---|---|
| 7,232,806 B2 * | 6/2007 | Tuschl et al. | ................ 514/44 A |
| 2005/0182005 A1 * | 8/2005 | Tuschl et al. | .................... 514/44 |
| 2005/0261218 A1 | 11/2005 | Esau et al. | |
| 2009/0004668 A1 * | 1/2009 | Chen et al. | ........................ 435/6 |

OTHER PUBLICATIONS

Crooke, S., Ann. Rev. Medicine, vol. 55, pp. 61-95 (2004).*
Peracchi et al., Rev. Med. Virol., vol. 14, pp. 47-64 (2004).*
Agrawal et al., Molecular Med. Today, vol. 6, pp. 72-81 (2000).*
Chirila et al., Biomaterials, vol. 23, pp. 321-342 (2002).*
Opalinska et al., Nature rev., vol. 1, pp. 503-514 (2002).*
Doench et al., Genes and Development, vol. 18, No. 5, pp. 504-511 (2004).*
Holen et al, Nucleic Acids Res., vol. 30, No. 8, pp. 1757-1766 (2002).*
Jang et al., Expert Rev. Medical Devices, vol., No. 1, pp. 127-138 (2004).*
Rosenberg et al., J. Cell Biol., vol. 175, No. 1, pp. 77-85 (2006).*
Paroo et al., Trends in Biotechnology, vol. 22, No. 8, pp. 390-394 (2004).*
Callis et al. "Muscling through the microRNA world", Exp. Biol Med; Feb. 2008, vol. 233, No. 2, pp. 131-138. p. 132, right col. para 2, ln 1-4.
McCarthy, "The skeletal muscle-specific myomiR", Biochimica Biochim Biophys Acta. Nov. 2008;1779(11):682-91. Epub Mar. 12, 2008.
Miura P, Jasmin BJ. "Utrophin upregulation for treating Duchenne or Becker muscular dystrophy: how close are we?" Trends Mol Med. Mar. 2006;12:122-129.
Abuchowski, A., et al. "Immunosuppresive properties and circulating life of achromobacter glutaminase-asparaginase covalently attached to polyetholene glycol in man" Cancer Treat. Rep. 65: 1077-1081, 1981.
Buchwald, H, et al. Long-term continuous intravenous heparin administration by an implantable infusion pump in ambulatory patients with recurrent venous thrombosis. Surgery 1980; 88:507-516.
Goodson, *Medical Applications of Controlled Release*, vol. II, Chapter 7 pp. 115-138 (1984).
Saudek et al., "A Preliminary Trial of the Programmable Implantable Medication System for Insulin Delivery", N. Engl. J. Med. 321:574-579 (1989).
Sefton, MV, "Implantable pumps", Critical Reviews in Biomedical Engineering 14(3):201-240 (1987).
Langer et al. "New methods of drug delivery" Science vol. 249 No. 4976 pp. 1527-1533 Sep. 28, 1990.
Katre et al., "Chemical modification of recombinant interleukin 2 by polyethylene glycol increases its potency in the murine Meth A sarcoma model", Proc. Natl. Acad. Sci.1987, vol. 84, pp. 1487-1491.

* cited by examiner

*Primary Examiner* — Jane Zara
(74) *Attorney, Agent, or Firm* — Mark S. Cohen; Pearl Cohen Zedek Latzer Baratz LLP

(57) ABSTRACT

This invention provides a method for enhancing utrophin protein production in a cell by inhibiting an utrophin microRNA molecule. Moreover, the invention provides that methods for enhancing utrophin protein production in a muscle cell are used for treating a muscular dystrophy and/or other myopathies.

1 Claim, 11 Drawing Sheets

SEQUENCE LISTING

```
<160> NUMBER OF SEQ ID NOS: 23

<210> SEQ ID NO 1
<211> LENGTH: 22
<212> TYPE: RNA
<213> ORGANISM: Homo sapiens

<400> SEQUENCE: 1
ugagguagua gguuguaugg uu                                             22

<210> SEQ ID NO 2
<211> LENGTH: 22
<212> TYPE: RNA
<213> ORGANISM: Homo sapiens

<400> SEQUENCE: 2
aaccauacaa ccuacuaccu ca                                             22

<210> SEQ ID NO 3
<211> LENGTH: 22
<212> TYPE: RNA
<213> ORGANISM: Homo sapiens
```

-continued

```
<400> SEQUENCE: 3
uuuggucccc uucaaccagc ua                                              22

<210> SEQ ID NO 4
<211> LENGTH: 21
<212> TYPE: RNA
<213> ORGANISM: Homo sapiens

<400> SEQUENCE: 4
uagcugguug aagggggacca a                                              21

<210> SEQ ID NO 5
<211> LENGTH: 22
<212> TYPE: RNA
<213> ORGANISM: Homo sapiens

<400> SEQUENCE: 5
ucucccaacc cuuguaccag ug                                              22

<210> SEQ ID NO 6
<211> LENGTH: 22
<212> TYPE: RNA
<213> ORGANISM: Homo sapiens

<400> SEQUENCE: 6
cacugguaca aggguuggga ga                                              22

<210> SEQ ID NO 7
<211> LENGTH: 22
<212> TYPE: RNA
<213> ORGANISM: Homo sapiens

<400> SEQUENCE: 7
uagguaguuu ccuguuguug gg                                              22

<210> SEQ ID NO 8
<211> LENGTH: 21
<212> TYPE: RNA
<213> ORGANISM: Homo sapiens

<400> SEQUENCE: 8
ccaacaacag gaaacuaccu a                                               21

<210> SEQ ID NO 9
<211> LENGTH: 22
<212> TYPE: RNA
<213> ORGANISM: Homo sapiens

<400> SEQUENCE: 9
uggaauguaa ggaagugugu gg                                              22

<210> SEQ ID NO 10
<211> LENGTH: 22
<212> TYPE: RNA
<213> ORGANISM: Homo sapiens

<400> SEQUENCE: 10
ccacacacuu ccuuacauuc ca                                              22

<210> SEQ ID NO 11
<211> LENGTH: 21
<212> TYPE: RNA
<213> ORGANISM: Homo sapiens
```

<400> SEQUENCE: 11 agggccccccc cucaauccug u                                       21

<210> SEQ ID NO 12
<211> LENGTH: 21
<212> TYPE: RNA
<213> ORGANISM: Homo sapiens

<400> SEQUENCE: 12
acaggauuga gggggggccc u                                        21

<210> SEQ ID NO 13
<211> LENGTH: 2391
<212> TYPE: DNA
<213> ORGANISM: Homo sapiens

<400> SEQUENCE: 13
tgagcatcta tccagccagc caacatttcc cgaccttcag tattgccctc ttctgcaaat     60
gccaatccca agacccattc aaccccaaag ctccgtggct ccacgacaca agctgttgag    120
tgcttactgg gtgttctact gagggaacca acactgact atccaaagag aaaaggatat    180
tttggttttc taataacgta tattattgtt ttcttctccc ctttctatgc aactgtaaat    240
taatgaacag agaagtattt ggaggtggta aagcatttgt cactgatttg tataatatat    300
acagccatgg gaaagtgggt gggggctttc taatatgaaa ctgtcttttt aataaccaag    360
agaaaaaatt gcataagaat tagaccactt tacattatta cattccttct gctgttcaca    420
ttaaccttgt acaataactt cacttattat ttgactgttt taccattatg ttttggttat    480
ttataaattt atcagccata caaacaaata gattctatgt atttgtttct ataatctggc    540
caaattccta agttcatata tttgaatcaa atatttaca tatgtggagt aggcaggcat    600
tctgaagata ctatttaact ttagttgacg tcacacacac catcctttag taaccactgg    660
atgactacac taaaaatcct gtggacttta acggcaagct gctggggtat ttttcctcct    720
gttttttattc cttttttgta agtagatctt gacgtcttta tttatttcat cttgcaatct    780
ctataataaa gaagactgta ttgtaatagt ctcaaaaaat tattttacca agggttacca    840
tttaagcata ttttcatttt gattcagaaa ccaaagttgg tacaacctct cctagtacat    900
gcaaccttgg ttttcatgag aaaacacacg gcaggccttt gcccattgtg aggagagcac    960
acatcatgct cttcagtttc cttttgaatag acttttattg ttgttttttgt attttttcgag   1020
tcctgtgtaa gttttgaaag ctctggttgt ttccttttgtg aaagcaggca gatacttagt   1080
tggctgtctc atttgaagct ttggagcaga tagtcagatg tctcatgacc cctcacttgg   1140
ccagcagcac atccgagaag gatgtcactc acaagcctac accacggctt ctctagaatg   1200
aaatcagtgc tcggatgatt gtatccctgc ctctacttct gagtgtgttc aactaggtat   1260
tggcttcttt ttcttttttct tttctttttt ttttaattta acacttaatt gccgatttta   1320
gagaaaccaa aaataaaggt gaaggtaata tgttttgatt caaacatata tgcttttaaa   1380
catcagacat gctaactttg gttctctttta ctggaatctg gcccagagga ggtgaaattt   1440
agaaatgtta ttctttagat gggtgggtgg gttgggggggc caagggtgtc tattttccag   1500
cattagatat ttttgagacg aagaaaattg ttttatataa ggggagagcc atgatcacct   1560
ttctacctca gaaccacctt cctccattgt gttggacata gctttatatg ccgcagtgtg   1620
caaaacctag ggctgtagtc aggcctttcc atacccagga agcacctgtg taagaagat    1680

-continued

```
caacagaaac tcccggaact cagaacccca agttgtagat ttggtgtcgt ccttgttctt    1740
gctttgagga gtcatgtatt cttttatttc ctgcctgtat ttgtatgcaa aatgatctct    1800
atctgctatt acagaaaaag ctacacaaaa cactacattg taaccttctg agtaataaat    1860
aagaggaaat atattacagt aaccatgatg agaaataagt gtattgttct tttgaaatat    1920
gtggttaatc gcagactgtc atctaatctg ttacataccg tatttttcat cctgaataaa    1980
agtaatttta acacaaaatg actttgatgt ttggctgtgt tcagctgatg aaatcagatc    2040
tctgaatgta tgtgatgaaa gctaactata agatgatcta tattctgata aatctaaata    2100
ttttctgaaa ctctctctta tacattaatc tagtctccat tcactcatta tctctctctc    2160
ctttcttgca tataaatatg attatatatt tttcaatttc ctgtacaaat cagagtctta    2220
ttactaggga aaatggatgt tataagtaca ttcctaaagc ccattgggcc ttcatttta    2280 taacttggag ctactgagat ttatcaggtt actctctcaa atccacttc atcactagac    2340 tcatagtttt ctatgtatct atattattat aactaaataa aaatatacat g             2391
```

<210> SEQ ID NO 14
<211> LENGTH: 23
<212> TYPE: DNA
<213> ORGANISM: Homo sapiens

<400> SEQUENCE: 14

```
atgggaaagt gggtgggggc ttt                                              23
```

<210> SEQ ID NO 15
<211> LENGTH: 22
<212> TYPE: DNA
<213> ORGANISM: Homo sapiens

<400> SEQUENCE: 15

```
ccactttaca ttattacatt cc                                               22
```

<210> SEQ ID NO 16
<211> LENGTH: 20
<212> TYPE: DNA
<213> ORGANISM: Homo sapiens

<400> SEQUENCE: 16

```
atgggtgggt gggttggggg                                                  20
```

<210> SEQ ID NO 17
<211> LENGTH: 17
<212> TYPE: DNA
<213> ORGANISM: Homo sapiens

<400> SEQUENCE: 17

```
gtgggttggg gggccaa                                                     17
```

<210> SEQ ID NO 18
<211> LENGTH: 24
<212> TYPE: DNA
<213> ORGANISM: Homo sapiens

<400> SEQUENCE: 18

```
agccatgatc acctttctac ctca                                             24
```

<210> SEQ ID NO 19
<211> LENGTH: 19
<212> TYPE: DNA
<213> ORGANISM: Homo sapiens

```
<400> SEQUENCE: 19
ccatacccag gaagcacct                                              19

<210> SEQ ID NO 20
<211> LENGTH: 21
<212> TYPE: RNA
<213> ORGANISM: Homo sapiens

<400> SEQUENCE: 20
aaguggauau uguugccauc a                                           21

<210> SEQ ID NO 21
<211> LENGTH: 21
<212> TYPE: DNA
<213> ORGANISM: Homo sapiens

<400> SEQUENCE: 21
aguacugcuu acgauacggt t                                           21

<210> SEQ ID NO 22
<211> LENGTH: 21
<212> TYPE: DNA
<213> ORGANISM: Homo sapiens

<400> SEQUENCE: 22
ccguaucgua agcaguacut t                                           21

<210> SEQ ID NO 23
<211> LENGTH: 21
<212> TYPE: DNA
<213> ORGANISM: Homo sapiens

<400> SEQUENCE: 23
gggtgggtgg gttgggggc c                                            21
```

METHODS FOR ENHANCING UTROPHIN PRODUCTION VIA INHIBITION OF MICRORNA

CROSS-REFERENCE TO RELATED APPLICATIONS

This application is a National Phase Application of PCT International Application PCT/US09/041783, filed Apr. 27, 2009, claiming priority to U.S. Patent Application 61/071,408, filed Apr. 28, 2008, which is incorporated by reference herein in its entirety.

FIELD OF THE INVENTION

The invention relates to methods for enhancing utrophin protein production and methods for treating myopathies. Specifically, the invention relates to enhancing utrophin protein translation by inhibiting microRNAs.

BACKGROUND OF THE INVENTION

Duchenne Muscular Dystrophy (DMD) is one of a group of muscular dystrophies characterized by the enlargement of muscles. DMD is one of the most prevalent types of muscular dystrophy and is characterized by rapid progression of muscle degeneration which occurs early in life. DMD is X-linked and affect mainly males—an estimated 1 in 3,500 boys worldwide.

The gene for DMD, found on the X chromosome, encodes a large protein—dystrophin. Dystrophin is required inside muscle cells for structural support: it is thought to strengthen muscle cells by anchoring elements of the internal cytoskeleton to the surface membrane and external structures. Without it, the muscle cannot produce force effectively and is susceptible to damage during contraction, eventually leading to muscle death and replacement by fatty and fibrous tissue. The accompanying immune response can add to the damage.

A mouse model for DMD exists, and is proving useful for furthering our understanding on both the normal function of dystrophin and the pathology of the disease. In particular, initial experiments that enhance the production of utrophin, a dystrophin relative, in order to compensate for the loss of dystrophin in the mouse are promising, and may lead to the development of effective therapies for this devastating disease. Accordingly, a need exists for enhancing utrophin production in order to treat muscular dystrophies and other myopathies.

MicroRNAs (miRNAs) are small, RNA molecules encoded in the genomes of plants and animals. These highly conserved, ~21-mer RNAs regulate the expression of genes by binding to the 3' or 5'-untranslated regions (3'-UTR or 5'-UTR) of specific mRNAs.

Although the first published description of an miRNA appeared ten years ago, only in the last two to three years has the breadth and diversity of this class of small, regulatory RNAs been appreciated. A great deal of effort has gone into understanding how, when, and where miRNAs are produced and function in cells, tissues, and organisms. Each miRNA is thought to regulate multiple genes, and since hundreds of miRNA genes are predicted to be present in higher eukaryotes the potential regulatory circuitry afforded by miRNA is enormous.

MicroRNAs may act as key regulators of processes as diverse as early development, cell proliferation and cell death, apoptosis and fat metabolism, and cell differentiation. Recent studies of microRNA expression implicate microRNAs in brain development chronic lymphocytic leukemia, colonic adenocarcinoma, Burkett's Lymphoma, and viral infection suggesting possible links between miRNAs and viral disease, neurodevelopment, and cancer. miRNAs are differentially expressed in myopathies and have been implicated in heart disease. Accordingly, a need exists for determining the role of microRNAs in utrophin production in order to treat myopathies or utrophin mediated diseases.

SUMMARY OF THE INVENTION

In one embodiment, the present invention provides a method for enhancing utrophin protein production in a cell, the method comprising the step of inhibiting utrophin microRNA molecule, thereby enhancing utrophin protein production in a cell.

In another embodiment, the present invention provides a method for treating a muscular dystrophy, in a subject, the method comprising the step of administering to said subject a composition for inhibiting utrophin microRNA molecule, thereby treating said muscular dystrophy in said subject. In an exemplary embodiment, said muscular dystrophy is Duchenne Muscular Dystrophy (DMD).

In another embodiment, the present invention provides a method for reducing the symptoms associated with a muscular dystrophy, in a subject, comprising the step of administering to said subject a composition for inhibiting utrophin microRNA molecule, thereby reducing the symptoms associated with said muscular dystrophy in said subject.

In another embodiment, the present invention provides a method for treating a muscle disease in a subject, comprising the step of administering to said subject a composition for inhibiting utrophin microRNA molecule, thereby treating said disease in said subject.

In another embodiment, the present invention provides a composition comprising an effective amount of an agent that inhibits utrophin microRNA molecule. In an exemplary embodiment, the agent comprises a let-7c antisense molecule, a miR-196b antisense molecule, a miR-133b antisense molecule, a miR-150 antisense molecule, a miR-206 antisense molecule, or a miR-296-5p antisense molecule.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

Figure 1:
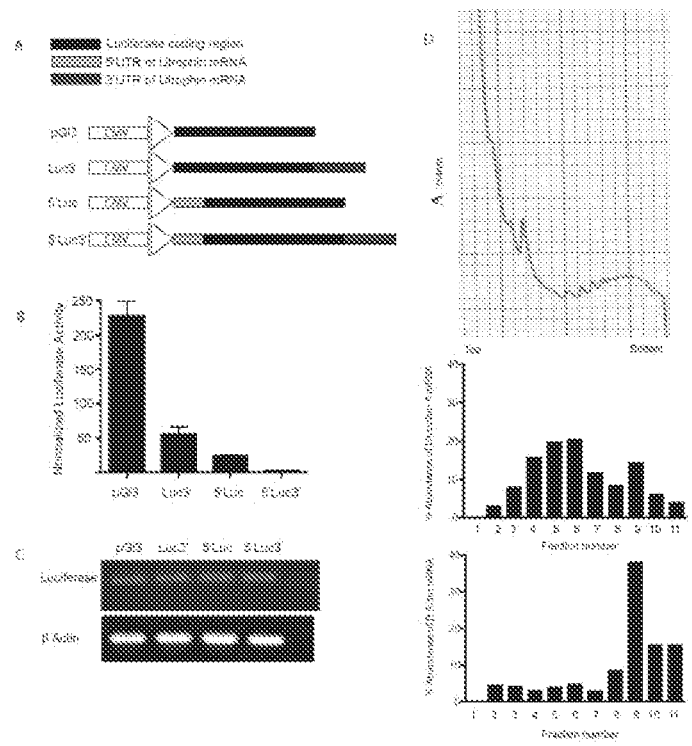
FIG. 1 shows the utrophin UTR-luciferase constructs used in C2C12 cells (A); a bar graph showing the luciferase activity in the transfected C2C12 cells (B); a gel showing mRNA expression in C2C12 of luciferase and β-actin by RT-PCR (C); a graph showing ribosomal profiling of utrophin-A mRNA in C2C12 cells by sucrose density gradient analysis (D). C2C12 cell extract was resolved on a sucrose density gradient, collected into eleven fractions, and the target mRNA level in each fraction was determined (D).

In one embodiment, provided herein is a method of enhancing utrophin protein production in a cell, comprising the step of inhibiting utrophin microRNA molecule, thereby enhancing utrophin protein production in a cell. In another embodiment, the cell is a muscle cell.

In another embodiment, provided herein is a method of enhancing utrophin protein production in a cell, comprising the step of contacting a microRNA molecule that binds an utrophin mRNA with an inhibitor, thereby enhancing utrophin protein production in a cell. In another embodiment, the cell is a muscle cell.

In another embodiment, provided herein is a method of enhancing utrophin protein production in a cell, comprising the step of contacting a microRNA molecule that binds an utrophin mRNA 3' UTR with an inhibitor, thereby enhancing utrophin protein production in a cell. In another embodiment, the cell is a muscle cell.

In another embodiment, provided herein is a method of enhancing utrophin protein production in a cell, comprising the step of contacting a microRNA molecule that binds an utrophin mRNA 5' UTR with an inhibitor, thereby enhancing utrophin protein production in a cell. In another embodiment, the cell is a muscle cell.

In another embodiment, provided herein is a method of enhancing utrophin protein production in a cell, comprising the step of contacting a microRNA molecule that binds an utrophin mRNA 3' UTR with an antisense molecule which inhibits the binding of the microRNA molecule to a 3' UTR utrophin mRNA, thereby enhancing utrophin protein production in a cell. In another embodiment, the cell is a muscle cell.

In another embodiment, provided herein is a method of enhancing utrophin protein production in a cell, comprising the step of contacting a microRNA molecule that binds an utrophin mRNA 5' UTR with an antisense molecule which inhibits the binding of the microRNA molecule to a 5' UTR utrophin mRNA, thereby enhancing utrophin protein production in a cell. In another embodiment, the cell is a muscle cell.

In another embodiment, provided herein is a method of enhancing utrophin protein production in a cell, comprising the step of contacting a muscle cell specific microRNA molecule that binds an utrophin mRNA 3' UTR with an inhibitor, thereby enhancing utrophin protein production in a cell. In another embodiment, the cell is a muscle cell.

In another embodiment, provided herein is a method of enhancing utrophin protein production in a cell, comprising the step of contacting a muscle cell specific microRNA molecule that binds an utrophin mRNA 5' UTR with an inhibitor, thereby enhancing utrophin protein production in a cell. In another embodiment, the cell is a muscle cell.

In another embodiment, provided herein is a method of enhancing utrophin protein production in a cell, comprising the step of contacting a muscle cell specific microRNA molecule that binds an utrophin mRNA 3' UTR with an antisense molecule which inhibits the binding of the microRNA molecule to a 3' UTR utrophin mRNA, thereby enhancing utrophin protein production in a cell. In another embodiment, the cell is a muscle cell.

In another embodiment, provided herein is a method of enhancing utrophin protein production in a cell, comprising the step of contacting a muscle cell specific microRNA molecule that binds an utrophin mRNA 5' UTR with an antisense molecule which inhibits the binding of the microRNA molecule to a 5' UTR utrophin mRNA, thereby enhancing utrophin protein production in a cell. In another embodiment, the cell is a muscle cell.

In another embodiment, utrophin mRNA 3' UTR comprises the nucleotide sequence:

(SEQ ID NO: 13)

```
TGAGCATCTATCCAGCCAGCCAACATTTCCCGACCTTCAGTATTGCCCTCTTCTGCAAATGCCAATCCCAAGACCC
ATTCAACCCCAAAGCTCCGTGGCTCCACGACACAAGCTGTTGAGTGCTTACTGGGTGTTCTACTGAGGGAACCAA
ACACTGACTATCCAAAGAGAAAAGGATATTTTGGTTTTCTAATAACGTATATTATTGTTTTCTTCTCCCCTTTCTAT
GCAACTGTAAATTAATGAACAGAGAAGTATTTGGAGGTGGTAAAGCATTTGTCACTGATTTGTATAATATATACA
GCCATGGGAAAGTGGGTGGGGGCTTTCTAATATGAAACTGTCTTTTTAATAACCAAGAGAAAAAATTGCATAAG
AATTAGACCACTTTACATTATTACATTCCTTCTGCTGTTCACATTAACCTTGTACAATAACTTCACTTATTATTTGA
CTGTTTTACCATTATGTTTTGGTTATTTATAAATTTATCAGCCATACAAACAAATAGATTCTATGTATTTGTTTCTA
TAATCTGGCCAAATTCCTAAGTTCATATATTTGAATCAAATATTTTACATATGTGGAGTAGGCAGGCATTCTGAAG
ATACTATTTAACTTTAGTTGACGTCACACACACCATCCTTTAGTAACCACTGGATGACTACACTAAAAATCCTGTG
GACTTTAACGGCAAGCTGCTGGGGTATTTTTCCTCCTGTTTTTATTCCTTTTTTGTAAGTAGATCTTGACGTCTTTAT
TTATTTCATCTTGCAATCTCTATAATAAAGAAGACTGTATTGTAATAGTCTCAAAAAATTATTTTACCAAGGGTTA
CCATTTAAGCATATTTTCATTTTGATTCAGAAACCAAAGTTGGTACAACCTCTCCTAGTACATGCAACCTTGGTTT
TCATGAGAAAACACACGGCAGGCCTTTGCCCATTGTGAGGAGAGCACACATCATGCTCTTCAGTTTCCTTTGAAT
AGACTTTTATTGTTGTTTTGTATTTTTCGAGTCCTGTGTAAGTTTTGAAAGCTCTGGTTGTTTCCTTTGTGAAAGC
AGGCAGATACTTAGTTGGCTGTCTCATTTGAAGCTTTGGAGCAGATAGTCAGATGTCTCATGACCCCTCACTTGGC
CAGCAGCACATCCGAGAAGGATGTCACTCACAAGCCTACACCACGGCTTCTCTAGAATGAAATCAGTGCTCGGAT
GATTGTATCCCTGCCTCTACTTCTGAGTGTGTTCAACTAGGTATTGGCTTCTTTTTCTTTTTCTTTTCTTTTTTTTTA
ATTTAACACTTAATTGCCGATTTTAGAGAAACCAAAAATAAAGGTGAAGGTAATATGTTTTGATTCAAACATATA
TGCTTTTAAACATCAGACATGCTAACTTTGGTTCTCTTTACTGGAATCTGGCCCAGAGGAGGTGAAATTTAGAAAT
GTTATTCTTTAGATGGGTGGGTGGGTTGGGGGGCCAAGGGTGTCTATTTTCCAGCATTAGATATTTTTGAGACGAA
GAAAATTGTTTTATATAAGGGGAGAGCCATGATCACCTTTCTACCTCAGAACCACCTTCCTCCATTGTGTTGGACA
TAGCTTTATATGCCGCAGTGTGCAAAACCTAGGGCTGTAGTCAGGCCTTTCCATACCCAGGAAGCACCTGTGTAA
AGAAGATCAACAGAAACTCCCGGAACTCAGAACCCCAAGTTGTAGATTTGGTGTCGTCCTTGTTCTTGCTTTGAG
GAGTCATGTATTCTTTTATTTCCTGCCTGTATTTGTATGCAAAATGATCTCTATCTGCTATTACAGAAAAAGCTACA
CAAAACACTACATTGTAACCTTCTGAGTAATAAATAAGAGGAAATATATTACAGTAACCATGATGAGAAATAAG
TGTATTGTTCTTTTGAAATATGTGGTTAATCGCAGACTGTCATCTAATCTGTTACATACCGTATTTTTCATCCTGAA
TAAAAGTAATTTTAACACAAAATGACTTTGATGTTTGGCTGTGTTCAGCTGATGAAATCAGATCTCTGAATGTATG
TGATGAAAGCTAACTATAAGATGATCTATATTCTGATAAATCTAAATATTTTCTGAAACTCTCTCTTATACATTAA
TCTAGTCTCCATTCACTCATTATCTCTCTCCTTTCTTGCATATAAATATGATTATATATTTTTCAATTTCCTGTAC
AAATCAGAGTCTTATTACTAGGGAAAATGGATGTTATAAGTACATTCCTAAAGCCCATTGGGCCTTCATTTTTATA
ACTTGGAGCTACTGAGATTTATCAGGTTACTCTCTCAAATCCACTTTCATCACTAGACTCATAGTTTTCTATGTATC
TATATTATTATAACTAAATAAAAATATACATG.
```

In another embodiment, the utrophin mRNA 3' UTR nucleic acid sequence is a homologue, a variant, or a functional fragment of SEQ ID NO: 13. Each possibility represents a separate embodiment of the present invention.

In another embodiment, a microRNA of the invention inhibits utrophin protein production by binding to an utrophin 3' UTR binding sequence. In another embodiment, a microRNA of the invention inhibits utrophin protein production by binding to a specific sequence within utrophin 3' UTR mRNA.

In another embodiment, miR-296-5p binding sequence in utrophin 3' UTR is: ATGGGAAAGTGGGTGGGGGCTTT (SEQ ID NO: 14). In another embodiment, miR-296-5p binding sequence in utrophin 3'UTR is: GGGTGGGTGGGTTGGGGGGCC (SEQ ID NO: 23). In another embodiment, miR-206 binding sequence in utrophin 3'UTR is: CCACTTTACATTATTACATTCC (SEQ ID NO: 15). In another embodiment, miR-150 binding sequence in utrophin 3'UTR is: ATGGGTGGGTGGGTTGGGGG (SEQ ID NO: 16). In another embodiment, miR-133b binding sequence in utrophin 3'UTR is: GTGGGTTGGGGGGCCAA (SEQ ID NO: 17). In another embodiment, let-7c binding sequence in utrophin 3'UTR is: AGCCATGATCACCTTTCTACCTCA (SEQ ID NO: 18). In another embodiment, miR-196b binding sequence in utrophin 3'UTR is: CCATACCCAGGAAGCACCT (SEQ ID NO: 19).

In another embodiment, the cell is a skeletal muscle cell. In another embodiment, the cell is a smooth muscle cell. In another embodiment, the cell is a satellite muscle cell. In another embodiment, the cell is a cardiac muscle cell.

In another embodiment, a microRNA molecule is a muscle cell specific microRNA molecule. In another embodiment, a microRNA molecule binds to utrophin. In another embodiment, a microRNA molecule binds to specifically to utrophin. In another embodiment, a microRNA molecule is complementary to an utrophin RNA sequence. In another embodiment, a microRNA molecule is complementary to a 5' untranslated region (UTR) of an utrophin RNA sequence. In another embodiment, a microRNA molecule is complementary to a 3' UTR of an utrophin RNA sequence. In another embodiment, a microRNA molecule decreases the levels of utrophin protein. In another embodiment, a microRNA molecule decreases the levels of utrophin protein without decreasing the utrophin mRNA. In another embodiment, a microRNA molecule targets utrophin-A IRES. In another embodiment, a microRNA molecule targets utrophin-A IRES in a muscle cell. In another embodiment, a microRNA molecule represses utrophin-A IRES activity (FIGS. 3 and 7-9).

In another embodiment, a microRNA molecule is a muscle cell specific microRNA molecule. In another embodiment, the microRNA molecule is miR-206. In another embodiment, the microRNA molecule is miR-1. In another embodiment, the microRNA molecule is miR-133. In another embodiment, the microRNA molecule is let-7c. In another embodiment, the microRNA molecule is miR-196b. In another embodiment, the microRNA molecule is miR-133b. In another embodiment, the microRNA molecule is miR-150. In another embodiment, the microRNA molecule is miR-296-5p.

In another embodiment, the sequence of Let-7c microRNA (mouse and human) is: 5'-UGAGGUAGUAGGUUGUAUG-GUU-3' (SEQ ID NO: 1). In another embodiment, the sequence of Let-7c microRNA inhibitor or anti-Let-7c is: 5'-AACCAUACAACCUACUACCUCA-3'(SEQ ID NO: 2).

In another embodiment, the sequence of miR-133b microRNA (mouse and human) is: 5'-UUUGGUCCCCUU-CAACCAGCUA-3' (SEQ ID NO: 3). In another embodiment, the sequence of miR-133b microRNA inhibitor or anti-miR-133b is: 5'-UAGCUGGUUGAAGGGGACCAA-3' (SEQ ID NO: 4).

In another embodiment, the sequence of miR-150 microRNA (mouse and human) is: 5'-UCUCCCAACCCUU-GUACCAGUG-3' (SEQ ID NO: 5). In another embodiment, the sequence of miR-150 microRNA inhibitor or anti-miR-150 is: 5'-CACUGGUACAAGGGUUGGGAGA-3' (SEQ ID NO: 6).

In another embodiment, the sequence of miR-196b microRNA (mouse and human) is: 5'-UAGGUAGUUUC-CUGUUGUUGGG-3' (SEQ ID NO: 7). In another embodiment, the sequence of miR-196b microRNA inhibitor or anti-miR-196b is: 5'-CCAACAACAGGAAACUACCUA-3' (SEQ ID NO: 8).

In another embodiment, the sequence of miR-206 microRNA (mouse and human) is: 5'-UGGAAUGUAAG-GAAGUGUGUGG-3' (SEQ ID NO: 9). In another embodiment, the sequence of miR-206 microRNA inhibitor or anti-miR-206 is: 5'-CCACACACUUCCUUACAUUCCA-3' (SEQ ID NO: 10).

In another embodiment, the sequence of miR-296-5p microRNA (mouse and human) is: 5'-AGGGCCCCCCCU-CAAUCCUGU-3' (SEQ ID NO: 11). In another embodiment, the sequence of miR-296-5p microRNA inhibitor or anti-miR-296-5p is: 5'-ACAGGAUUGAGGGGGGGCCCU-3' (SEQ ID NO: 12).

In another embodiment, the microRNA molecule miR-206 comprises the sequence of miRBase (http://microrna.sanger.ac.uk/sequences/) accession number MI0000249. In another embodiment, the microRNA molecule miR-206 comprises the sequence of miRBase accession number MI0000490. In another embodiment, the microRNA molecule miR-206 comprises the sequence of miRBase accession number MI0000948. In another embodiment, the microRNA molecule miR-206 comprises the sequence of miRBase accession number MI0001207. In another embodiment, the microRNA molecule miR-206 comprises the sequence of miRBase accession number MI0002045. In another embodiment, the microRNA molecule miR-206 comprises the sequence of miRBase accession number MI0002046. In another embodiment, the microRNA molecule miR-206 comprises the sequence of miRBase accession number MI0002619. In another embodiment, the microRNA molecule miR-206 comprises the sequence of miRBase accession number MI0002620. In another embodiment, the microRNA molecule miR-206 comprises the sequence of miRBase accession number MI0004863. In another embodiment, the microRNA molecule miR-206 comprises the sequence of miRBase accession number MI0005317. In another embodiment, the microRNA molecule miR-206 comprises the sequence of miRBase accession number MI0007667. In another embodiment, the microRNA molecule miR-206 comprises the sequence of miRBase accession number MI0008002.

In another embodiment, the microRNA molecule let-7c comprises the sequence of miRBase accession number MI0000064. In another embodiment, the microRNA molecule let-7c comprises the sequence of miRBase accession number MI0000559. In another embodiment, the microRNA molecule let-7c comprises the sequence of miRBase accession number MI0000560. In another embodiment, the microRNA molecule let-7c comprises the sequence of miRBase accession number MI0000830. In another embodiment, the microRNA molecule let-7c comprises the sequence of miRBase accession number MI0000831. In another embodiment, the microRNA molecule let-7c comprises the sequence of miRBase accession number MI0001174. In another embodiment, the microRNA molecule let-7c comprises the sequence of miRBase accession number MI0001866. In another embodiment, the microRNA molecule let-7c comprises the sequence of miRBase accession number MI0001867. In another embodiment, the microRNA molecule let-7c comprises the sequence of miRBase accession number MI0002445. In another embodiment, the microRNA molecule let-7c comprises the sequence of miRBase accession number MI0004886. In another embodiment, the microRNA molecule let-7c comprises the sequence of miRBase accession number MI0005124. In another embodiment, the microRNA molecule let-7c comprises the sequence of miRBase accession number MI0005454. In another embodiment, the microRNA molecule let-7c comprises the sequence of miRBase accession number MI0007138. In another embodiment, the microRNA molecule let-7c comprises the sequence of miRBase accession number MI0007152. In another embodiment, the microRNA molecule let-7c comprises the sequence of miRBase accession number MI0007183. In another embodiment, the microRNA molecule let-7c comprises the sequence of miRBase accession number MI0007184. In another embodiment, the microRNA molecule let-7c comprises the sequence of miRBase accession number MI0007574. In another embodiment, the microRNA molecule let-7c comprises the sequence of miRBase accession number MI0008076.

In another embodiment, the microRNA molecule miR-196b comprises the sequence of miRBase accession number MI0001150. In another embodiment, the microRNA molecule miR-196b comprises the sequence of miRBase accession number MI0001151. In another embodiment, the microRNA molecule miR-196b comprises the sequence of miRBase accession number MI0001152. In another embodiment, the microRNA molecule miR-196b comprises the sequence of miRBase accession number MI0002036. In another embodiment, the microRNA molecule miR-196b comprises the sequence of miRBase accession number MI0003365. In another embodiment, the microRNA molecule miR-196b comprises the sequence of miRBase accession number MI0003366. In another embodiment, the microRNA molecule miR-196b comprises the sequence of miRBase accession number MI0004943. In another embodiment, the microRNA molecule miR-196b comprises the sequence of miRBase accession number MI0005313. In another embodiment, the microRNA molecule miR-196b comprises the sequence of miRBase accession number MI0007660. In another embodiment, the microRNA molecule miR-196b comprises the sequence of miRBase accession number MI0008016.

In another embodiment, the microRNA molecule miR-133b comprises the sequence of miRBase accession number MI0000821. In another embodiment, the microRNA molecule miR-133b comprises the sequence of miRBase accession number MI0000822. In another embodiment, the microRNA molecule miR-133b comprises the sequence of miRBase accession number MI0001206. In another embodiment, the microRNA molecule miR-133b comprises the sequence of miRBase accession number MI0001994. In another embodiment, the microRNA molecule miR-133b comprises the sequence of miRBase accession number MI0003490. In another embodiment, the microRNA molecule miR-133b comprises the sequence of miRBase accession number MI0004837. In another embodiment, the microRNA molecule miR-133b comprises the sequence of miRBase accession number MI0007622.

In another embodiment, the microRNA molecule miR-150 comprises the sequence of miRBase accession number MI0000172. In another embodiment, the microRNA molecule miR-150 comprises the sequence of miRBase accession number MI0000479. In another embodiment, the microRNA molecule miR-150 comprises the sequence of miRBase accession number MI0000920. In another embodiment, the microRNA molecule miR-150 comprises the sequence of miRBase accession number MI0002016. In another embodiment, the microRNA molecule miR-150 comprises the sequence of miRBase accession number MI0004846. In another embodiment, the microRNA molecule miR-150 comprises the sequence of miRBase accession number MI0005058. In another embodiment, the microRNA molecule miR-150 comprises the sequence of miRBase accession number MI0007122. In another embodiment, the microRNA molecule miR-150 comprises the sequence of miRBase accession number MI0007123. In another embodiment, the microRNA molecule miR-150 comprises the sequence of miRBase accession number MI0007124. In another embodiment, the microRNA molecule miR-150 comprises the sequence of miRBase accession number MI0007125. In another embodiment, the microRNA molecule miR-150 comprises the sequence of miRBase accession number MI0007126. In another embodiment, the microRNA molecule miR-150 comprises the sequence of miRBase accession number MI0007127. In another embodiment, the microRNA molecule miR-150 comprises the sequence of miRBase accession number MI0007128. In another embodiment, the microRNA molecule miR-150 comprises the sequence of miRBase accession number MI0007641. In another embodiment, the microRNA molecule miR-150 comprises the sequence of miRBase accession number MI0007998.

In another embodiment, the microRNA molecule is miR-296-5p. In another embodiment, the microRNA molecule miR-296-5p comprises the sequence of miRBase accession number MI0000394. In another embodiment, the microRNA molecule miR-296-5p comprises the sequence of miRBase accession number MI0000747. In another embodiment, the microRNA molecule miR-296-5p comprises the sequence of miRBase accession number MI0007681.

In another embodiment, Utrophin upregulation is a potential therapeutic strategy for DMD. In another embodiment, Utrophin-A expression is repressed through the 5' and 3' UTRs by >98% at the translational level (FIG. 1). In another embodiment, Utrophin 3' UTR contains microRNA target sites. In another embodiment, Utrophin 5' UTR contains microRNA target sites. In another embodiment, Utrophin 3'UTR exhibits its inhibitory effect both on the IRES and on cap-dependent translation. In another embodiment, inhibition of microRNAs that target Utrophin UTRs is a potential therapeutic strategy for DMD.

In another embodiment, the method comprises inhibiting a microRNA molecule. In another embodiment, the method comprises inhibiting a microRNA molecule of the invention. In another embodiment, inhibiting a microRNA molecule comprises contacting a microRNA molecule with a complementary antisense oligonucleotide sequence. In another embodiment, inhibiting an utrophin microRNA molecule comprises contacting an utrophin microRNA molecule with an utrophin microRNA antisense molecule. In another embodiment, inhibiting an utrophin microRNA molecule comprises contacting an utrophin microRNA molecule with an antisense molecule that specifically binds to or hybridizes with the utrophin microRNA. An oligonucleotide analog "specifically hybridizes" to a target polynucleotide if the oligomer hybridizes to the target under physiological conditions, with a Tm substantially greater than 45° C., preferably at least 50° C., and typically 60° C.-80° C. or higher. Such hybridization preferably corresponds to stringent hybridization conditions. At a given ionic strength and pH, the Tm is the temperature at which 50% of a target sequence hybridizes to a complementary polynucleotide. Again, such hybridization may occur with "near" or "substantial" complementary of the antisense oligomer to the target sequence, as well as with exact complementarity.

In another embodiment, inhibiting let-7c, miR-196b, miR-133b, miR-150, miR-296-5p, miR-206 or any combination thereof leads to utrophin upregulation. In another embodiment, inhibitor of let-7c, miR-196b, miR-133b, miR-150, miR-296-5p, miR-296 or any combination thereof is used as a Duchenne muscular dystrophy therapeutic agent.

In another embodiment, an antisense specific molecule comprises at least 3 consecutive nucleotides which are complementary to an utrophin microRNA molecule or a fragment thereof. In another embodiment, an antisense specific molecule comprises at least 3 consecutive nucleotides which are complementary to a muscle cell utrophin microRNA molecule or a fragment thereof. In another embodiment, an antisense specific molecule comprises at least 3 consecutive nucleotides which are complementary to an utrophin microRNA molecule or a fragment thereof as described herein. In another embodiment, an antisense specific molecule comprises at least 3 consecutive nucleotides which are complementary to any microRNA molecule represented by a miRBase accession number as described hereinabove or a fragment thereof. In another embodiment, an antisense specific molecule comprises at least 4 consecutive nucleotides which are complementary to any microRNA molecule represented by a miRBase accession number as described hereinabove or a fragment thereof. In another embodiment, an antisense specific molecule comprises at least 5 consecutive nucleotides which are complementary to any microRNA molecule represented by a miRBase accession number as described hereinabove or a fragment thereof. In another embodiment, an antisense specific molecule comprises at least 7 consecutive nucleotides which are complementary to any microRNA molecule represented by a miRBase accession number as described hereinabove or a fragment thereof. In another embodiment, an antisense specific molecule comprises at least 9 consecutive nucleotides which are complementary to any microRNA molecule represented by a miRBase accession number as described hereinabove or a fragment thereof. In another embodiment, an antisense specific molecule comprises at least 11 consecutive nucleotides which are complementary to any microRNA molecule represented by a miRBase accession number as described hereinabove or a fragment thereof.

In another embodiment, an antisense specific molecule comprises at least 3 consecutive nucleotides derived from the 5' UTR or the 3' UTR of utrophin RNA molecule. In another embodiment, an antisense specific molecule comprises at least 4 consecutive nucleotides derived from the 5' UTR or the 3' UTR of utrophin RNA molecule. In another embodiment, an antisense specific molecule comprises at least 5 consecutive nucleotides derived from the 5' UTR or the 3' UTR of utrophin RNA molecule. In another embodiment, an antisense specific molecule comprises at least 6 consecutive nucleotides derived from the 5'UTR or the 3' UTR of utrophin RNA molecule. In another embodiment, an antisense specific molecule comprises at least 8 consecutive nucleotides derived from the 5' UTR or the 3' UTR of utrophin RNA molecule. In another embodiment, an antisense specific molecule comprises at least 10 consecutive nucleotides derived from the 5' UTR or the 3' UTR of utrophin RNA molecule. In another embodiment, an antisense specific molecule comprises at least 12 consecutive nucleotides derived from the 5' UTR or the 3'UTR of utrophin RNA molecule. In another embodiment, an antisense specific molecule comprises at least 14 consecutive nucleotides derived from the 5' UTR or the 3' UTR of utrophin RNA molecule. In another embodiment, an antisense specific molecule comprises a complementary sequence to any microRNA molecule represented by a miRBase accession number as described hereinabove or a fragment thereof. In another embodiment, an antisense specific molecule comprises a homologous complementary sequence to any microRNA molecule represented by a miRBase accession number as described hereinabove or a fragment thereof.

In another embodiment, a homologous complementary sequence is at least 60% homologous. In another embodiment, a homologous complementary sequence is at least 70% homologous. In another embodiment, a homologous complementary sequence is at least 80% homologous. In another embodiment, a homologous complementary sequence is at least 90% homologous. In another embodiment, a homologous complementary sequence is at least 95% homologous. In another embodiment, a homologous complementary sequence is at least 98% homologous. In another embodiment, a homologous complementary sequence is at least 99% homologous.

In another embodiment, an antisense specific molecule comprises at least 3 consecutive antisense nucleotides complementary to let-7c. In another embodiment, an antisense specific molecule comprises at least 5 consecutive antisense nucleotides complementary to let-7c. In another embodiment, an antisense specific molecule comprises at least 7 consecutive antisense nucleotides complementary to let-7c. In another embodiment, an antisense specific molecule comprises at least 9 consecutive antisense nucleotides complementary to let-7c. In another embodiment, an antisense specific molecule comprises at least 11 consecutive antisense nucleotides complementary to let-7c. In another embodiment, an antisense specific molecule comprises at least 13 consecutive antisense nucleotides complementary to let-7c.

In another embodiment, an antisense specific molecule comprises at least 3 consecutive antisense nucleotides complementary to miR-196b. In another embodiment, an antisense specific molecule comprises at least 5 consecutive antisense nucleotides complementary to miR-196b. In another embodiment, an antisense specific molecule comprises at least 7 consecutive antisense nucleotides complementary to miR-196b. In another embodiment, an antisense specific molecule comprises at least 9 consecutive antisense nucleotides complementary to miR-196b. In another embodiment, an antisense specific molecule comprises at least 11 consecutive antisense nucleotides complementary to miR-196b. In another embodiment, an antisense specific molecule comprises at least 13 consecutive antisense nucleotides complementary to miR-196b.

In another embodiment, an antisense specific molecule comprises at least 3 consecutive antisense nucleotides complementary to miR-133b. In another embodiment, an antisense specific molecule comprises at least 5 consecutive antisense nucleotides complementary to miR-133b. In another embodiment, an antisense specific molecule comprises at least 7 consecutive antisense nucleotides complementary to miR-133b. In another embodiment, an antisense specific molecule comprises at least 9 consecutive antisense nucleotides complementary to miR-133b. In another embodiment, an antisense specific molecule comprises at least 11 consecutive antisense nucleotides complementary to miR-133b. In another embodiment, an antisense specific molecule comprises at least 13 consecutive antisense nucleotides complementary to miR-133b.

In another embodiment, an antisense specific molecule comprises at least 3 consecutive antisense nucleotides complementary to miR-150. In another embodiment, an antisense specific molecule comprises at least 5 consecutive antisense nucleotides complementary to miR-150. In another embodiment, an antisense specific molecule comprises at least 7 consecutive antisense nucleotides complementary to miR-150. In another embodiment, an antisense specific molecule comprises at least 9 consecutive antisense nucleotides complementary to miR-150. In another embodiment, an antisense specific molecule comprises at least 11 consecutive antisense nucleotides complementary to miR-150. In another embodiment, an antisense specific molecule comprises at least 13 consecutive antisense nucleotides complementary to miR-150.

In another embodiment, an antisense specific molecule comprises at least 3 consecutive antisense nucleotides complementary to miR-296-5p. In another embodiment, an antisense specific molecule comprises at least 5 consecutive antisense nucleotides complementary to miR-296-5p. In another embodiment, an antisense specific molecule comprises at least 7 consecutive antisense nucleotides complementary to miR-296-5p. In another embodiment, an antisense specific molecule comprises at least 9 consecutive antisense nucleotides complementary to miR-296-5p. In another embodiment, an antisense specific molecule comprises at least 11 consecutive antisense nucleotides complementary to miR-296-5p. In another embodiment, an antisense specific molecule comprises at least 13 consecutive antisense nucleotides complementary to miR-296-5p.

In another embodiment, an antisense specific molecule comprises at least 3 consecutive antisense nucleotides complementary to miR-206. In another embodiment, an antisense specific molecule comprises at least 5 consecutive antisense nucleotides complementary to miR-206. In another embodiment, an antisense specific molecule comprises at least 7 consecutive antisense nucleotides complementary to miR-206. In another embodiment, an antisense specific molecule comprises at least 9 consecutive antisense nucleotides complementary to miR-206. In another embodiment, an antisense specific molecule comprises at least 11 consecutive antisense nucleotides complementary to miR-206. In another embodiment, an antisense specific molecule comprises at least 13 consecutive antisense nucleotides complementary to miR-206.

In another embodiment, an antisense specific molecule comprises a let-7c antisense molecule (e.g., a sequence set forth in SEQ ID NO: 2). In another embodiment, an antisense specific molecule comprises a miR-133b antisense molecule (e.g., a sequence set forth in SEQ ID NO: 4). In another embodiment, an antisense specific molecule comprises a miR-150 antisense molecule (e.g., a sequence set forth in SEQ ID NO: 6). In another embodiment, an antisense specific molecule comprises a miR-196b antisense molecule (e.g., a sequence set forth in SEQ ID NO: 8). In another embodiment, an antisense specific molecule comprises a miR-206 antisense molecule (e.g., a sequence set forth in SEQ ID NO: 10). In another embodiment, an antisense specific molecule comprises a miR-296-5p antisense molecule (e.g., a sequence set forth in SEQ ID NO: 12).

In another embodiment, an antisense molecule is siRNA. In another embodiment, siRNA is expressed by an appropriate vector. In another embodiment, siRNA is expressed by a plasmid. In another embodiment, siRNA transcription cassettes comprises an RNA polymerase III promoter (e.g. U6 or H1), which usually direct the transcription of small nuclear RNAs (snRNAs) (U6 is involved in gene splicing; H1 is the RNase component of human RNase P).

In another embodiment, an antisense molecule is a triple-helix-forming agent. In another embodiment, an antisense molecule is a ribozyme. In another embodiment, an antisense molecule is RNAi. In another embodiment, an antisense molecule is an antisense nucleic acid. In another embodiment, an antisense molecule is a triple helix forming agent which is circularized around a double-strand DNA to form a triple helix, thereby inhibiting transcription initiation.

In another embodiment, an antisense molecule is a synthetic peptide nucleic acids (PNAs). In another embodiment, an antisense molecule is an agRNA. In another embodiment, an antisense molecule is a LNA/DNA copolymer. In another embodiment, an antisense molecule is a small molecule chemical compound. In another embodiment, an antisense molecule as described herein is specific against a nucleotide sequence encoding an utrophin microRNA molecule.

In another embodiment, a ribozyme of the invention recognizes a specific nucleotide sequence in a microRNA molecule of the invention or a fragment thereof.

In another embodiment, the small molecule RNA used in the RNAi method is a double-strand RNA molecule homologous to the target microRNA. In another embodiment, the antisense nucleic acid is referred to as a DNA or RNA molecule at least partially complementary to the target microRNA molecule.

In another embodiment, the antisense nucleic acid is produced in the form of an oligonucleotide by a suitable method known to one skilled in the art. In another embodiment, the antisense oligonucleotide is produced by a chemical process, for example by the chemical phosphoamidite method comprising sulfuration with tetraethylthiuram disulfide in acetonitrile (Tetrahedron Lett., 1991, 32, 30005-30008). In another embodiment, the antisense nucleic acid is an oligoribonucleotides molecule. In another embodiment, the antisense nucleic acid is a 2'-O-methyl oligoribonucleotides molecule.

In another embodiment, provided herein is a method for treating a muscular dystrophy, in a subject, the method comprising the step of administering to said subject a composition for inhibiting utrophin microRNA molecule, thereby treating said muscular dystrophy in said subject.

In another embodiment, provided herein is a method for reducing the symptoms associated with a muscular dystrophy, in a subject, comprising the step of administering to said subject a composition for inhibiting utrophin microRNA molecule, thereby reducing the symptoms associated with said muscular dystrophy in said subject.

Muscular dystrophy may refer to any type of muscular dystrophy. In one embodiment, the muscular dystrophy is Duchenne Muscular Dystrophy (DMD). In another embodiment, the muscular dystrophy is Becker Muscular Dystrophy (BMD).

In another embodiment, provided herein is a method for treating a muscle disease in a subject, comprising the step of administering to said subject a composition for inhibiting utrophin microRNA molecule, thereby treating said disease in said subject.

The term "treatment" or "treating," as used herein, refers to any treatment of a disease in a mammal and includes: (1) preventing the disease from occurring in a mammal which may be predisposed to the disease but does not yet experience or display symptoms of the disease; e.g. prevention of the outbreak of the clinical symptoms; (2) inhibiting the disease, e.g., arresting its development; or (3) relieving the disease, e.g., causing regression of the symptoms of the disease.

Effective dosage for the treatment of a disease means that amount which, when administered to a mammal in need thereof, is sufficient to effect treatment, as defined above, for that disease. The method of treatment described herein can be used to treat any suitable mammal, preferably the mammal is a human.

The term "subject," as used herein, includes any human or non-human animal. The term "non-human animal" includes all vertebrates, e.g., mammals and non-mammals, such as non-human primates, sheep, dog, cow, chickens, amphibians, reptiles, etc.

In another embodiment, provided herein is a method of treating Duchene muscular dystrophy (DMD) in a subject, comprising the step of administering to said subject a composition for inhibiting utrophin microRNA molecule, thereby treating Duchene muscular dystrophy (DMD) in a subject. In another embodiment, provided herein is a method of reducing the symptoms associated with Duchenne muscular dystrophy (DMD) in a subject, comprising the step of administering to said subject a composition for inhibiting utrophin microRNA molecule, thereby reducing the symptoms associated with Duchenne muscular dystrophy (DMD) in a subject.

In another embodiment, provided herein is a method of treating Becker muscular dystrophy (BMD) in a subject, comprising the step of administering to said subject a composition for inhibiting utrophin microRNA molecule, thereby treating Becker muscular dystrophy (BMD) in a subject. In another embodiment, provided herein is a method of reducing the symptoms associated with Becker muscular dystrophy (BMD) in a subject, comprising the step of administering to said subject a composition for inhibiting utrophin microRNA molecule, thereby reducing the symptoms associated with Becker muscular dystrophy (BMD) in a subject.

In another embodiment, provided herein is a composition comprising an effective amount of an agent that inhibits utrophin microRNA molecule. In an exemplary embodiment, the agent comprises a let-7c antisense molecule (e.g., a sequence set forth in SEQ ID NO: 2), a miR-133b antisense molecule (e.g., a sequence set forth in SEQ ID NO: 4), a miR-150 antisense molecule (e.g., a sequence set forth in SEQ ID NO: 6), a miR-196b antisense molecule (e.g., a sequence set forth in SEQ ID NO: 8), a miR-206 antisense molecule (e.g., a sequence set forth in SEQ ID NO: 10), or a miR-296-5p antisense molecule (e.g., a sequence set forth in SEQ ID NO: 12).

In another embodiment, a composition for inhibiting utrophin microRNA molecule also induces utrophin protein production. In another embodiment, an utrophin microRNA molecule is a microRNA molecule which binds the 5' or 3' UTR of utrophin RNA and inhibits utrophin protein production.

In another embodiment, administering a composition for inhibiting utrophin microRNA molecule comprises contacting an utrophin microRNA molecule with an utrophin microRNA antisense specific molecule. In another embodiment, a composition for inhibiting utrophin microRNA molecule comprises an utrophin microRNA antisense molecule. In another embodiment, a composition for inhibiting utrophin microRNA molecule comprises an utrophin microRNA antisense specific molecule. In another embodiment, a composition for inhibiting a muscle cell specific microRNA molecule comprises an utrophin microRNA antisense specific molecule.

In another embodiment, a composition for inhibiting utrophin microRNA molecule is administered to a muscle cell in a subject. In another embodiment, a composition for inhibiting utrophin microRNA molecule is administered to a subject and is targeted to a muscle cell.

In another embodiment, the method of the present invention reduces symptoms associated with Duchenne muscular dystrophy (DMD) or Becker muscular dystrophy (BMD). In another embodiment, the method of the present invention improves walking of a DMD or BMD patient. In another embodiment, the method of the present invention reduces or inhibits calves swelling with fibrous tissue. In another embodiment, the methods of the present invention induce muscle growth. In another embodiment, the methods of the present invention induce muscle regeneration. In another embodiment, the method of the present invention reduces or inhibits contractures. In another embodiment, the method of the present invention reduces or inhibits scoliosis. In another embodiment, the method of the present invention reduces or inhibits diaphragm weakening. In another embodiment, the method of the present invention reduces or inhibits a cardiac disease caused by or associated with lack of dystrophin.

The inhibitors of the present invention and pharmaceutical compositions comprising same can be, in another embodiment, administered to a subject by any method known to a person skilled in the art, such as parenterally, paracancerally, transmucosally, transdermally, intramuscularly, intravenously, intra-dermally, subcutaneously, intra-peritonealy, intra-ventricularly, intra-cranially, intra-vaginally or intra-tumorally.

In another embodiment of methods and compositions of the present invention, the pharmaceutical compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In another embodiment of the present invention, the active ingredient is formulated in a capsule. In accordance with this embodiment, the compositions of the present invention comprise, in addition to the active compound (e.g. the mimetic compound, peptide or nucleotide molecule) and the inert carrier or diluent, a hard gelating capsule.

In another embodiment, the pharmaceutical compositions are administered by intravenous, intra-arterial, or intra-muscular injection of a liquid preparation. Suitable liquid formulations include solutions, suspensions, dispersions, emulsions, oils and the like. In another embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intra-muscularly and are thus formulated in a form suitable for intra-muscular administration.

In another embodiment, the pharmaceutical compositions are administered topically to body surfaces and are thus formulated in a form suitable for topical administration. Topical formulations include, in another embodiment, gels, ointments, creams, lotions, drops and the like.

In another embodiment, the pharmaceutical composition is administered as a suppository, for example a rectal suppository or a urethral suppository. In another embodiment, the pharmaceutical composition is administered by subcutaneous implantation of a pellet. In another embodiment, the pellet provides for controlled release of active agent over a period of time.

In another embodiment, the active compound is delivered in a vesicle, e.g. a liposome.

In other embodiments, carriers or diluents used in the composition of the present invention include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In other embodiments, pharmaceutically acceptable carriers for liquid formulations are aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of animal, vegetable, or synthetic origin, for example, peanut oil, soybean oil, olive oil, sunflower oil, fish-liver oil, another marine oil, or a lipid from milk or eggs.

In another embodiment, parenteral vehicles (for subcutaneous, intravenous, intra-arterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from milk or eggs.

In other embodiments, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCI, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants. Each of the above excipients represents a separate embodiment of the present invention.

In another embodiment, the pharmaceutical compositions provided herein are controlled-release compositions, i.e. compositions in which the active compound is released over a period of time after administration. Controlled- or sustained-release compositions include formulation in lipophilic depots (e.g. fatty acids, waxes, oils). In another embodiment, the composition is an immediate-release composition, i.e. a composition in which the active compound is released immediately after administration.

In another embodiment, the pharmaceutical composition is delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials are used; e.g. in microspheres in or an implant. In yet another embodiment, a controlled release system is placed in proximity to the target cell, thus requiring only a fraction of the systemic dose (see, e.g., Goodson, in Medical Applications of Controlled Release, supra, vol. 2, pp. 115-138 (1984); and Langer R, Science 249: 1527-1533 (1990).

The compositions also include, in another embodiment, incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also included in the present invention are particulate compositions coated with polymers (e.g. poloxamers or poloxamines) and the compound coupled to antibodies directed against tissue-specific receptors, ligands or antigens or coupled to ligands of tissue-specific receptors.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

Each of the above additives, excipients, formulations and methods of administration represents a separate embodiment of the present invention.

In one embodiment, the methods of the present invention comprise administering an active compound as the sole active ingredient. However, also encompassed within the scope of the present invention are methods for treating diseases and disorders that comprise administering the active compound in combination with one or more therapeutic agents. These agents include, but are not limited to, insulin agents, immunosuppressive agents, or drugs treating MS. In another embodiment, these agents are appropriate for the disease or disorder that is being treated, as is well known in the art.

In one embodiment, the methods of the present invention comprise administering an active compound as the sole active ingredient. However, also encompassed within the scope of the present invention are methods for treating diseases and disorders that comprise administering the active compound in combination with one or more therapeutic agents. These agents include, but are not limited to, insulin agents, immunosuppressive agents, or drugs treating MS. In another embodiment, these agents are appropriate for the disease or disorder that is being treated, as is well known in the art.

EXAMPLES

Example 1

Utrophin-A is Translated Inefficiently

Figure 2:
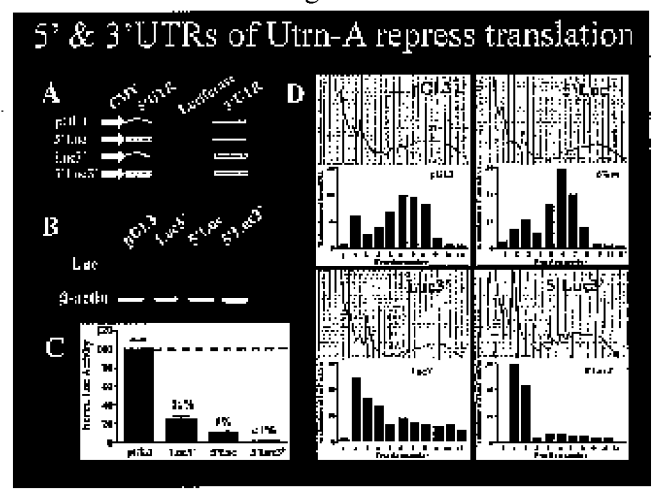
FIG. 2 shows that C2C12 cells were transfected with luciferase reporter constructs (A and B) and the mRNA levels and luciferase activity were analyzed (C). Also, C2C12 cell extract was resolved on a sucrose density gradient, collected into eleven fractions, and the target mRNA level in each fraction was determined by q-PCR analysis (D).
Figure 3:
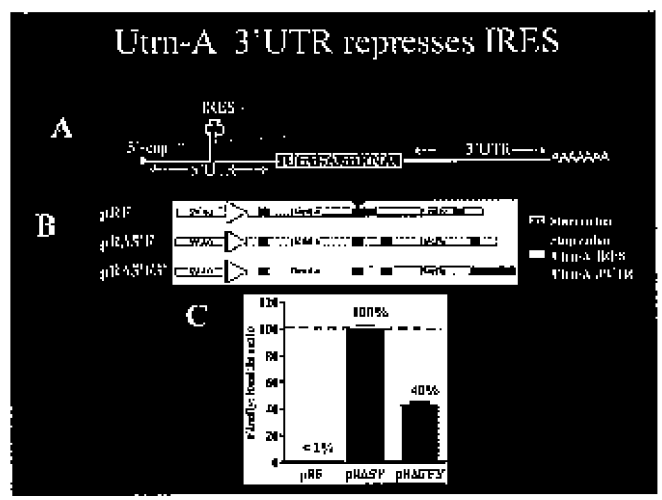
FIG. 3 shows that Utrophin 3' UTR represses IRES. (A) is a schematic representation of utrophin-A mRNA. 3 bicistronic constructs comprising control, utrophin IRES or utrophin IRES plus utrophin 3' UTR. (B) A bar graph showing the ratio of expression from the two cistrons, under the control of the 3 different constructs.
Figure 10:
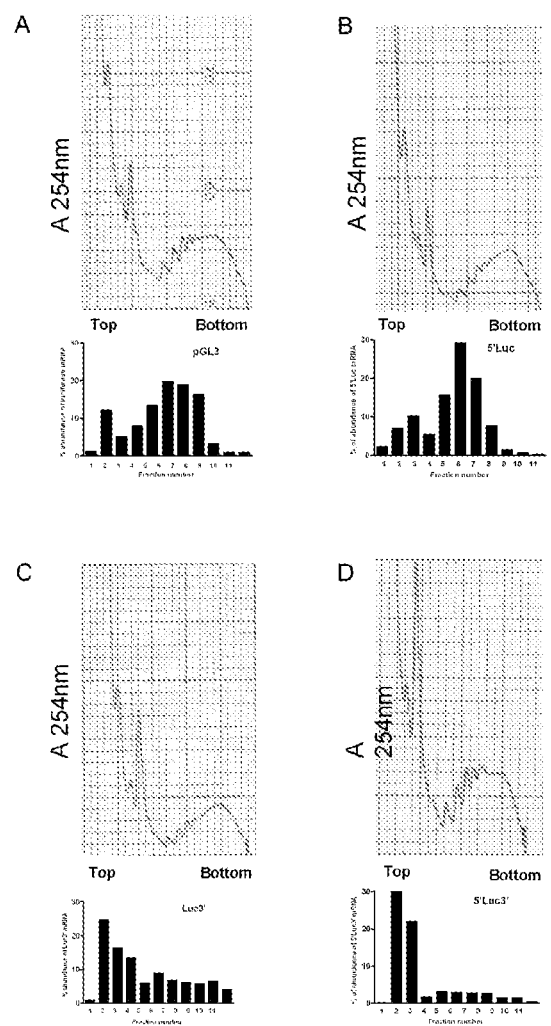
FIG. 10 shows that C2C12 cell extract was resolved on a sucrose density gradient, collected into eleven fractions, and the target mRNA level in each fraction was determined by q-PCR analysis and quantified as shown in the bar graphs for the constructs of FIG. 1.
Figure 11:
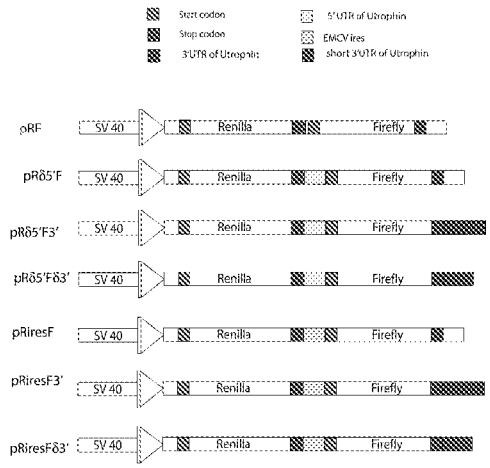
FIG. 11 shows that Utrophin 3' UTR represses IRES. The 7 bicistronic constructs comprising control, or utrophin-A or EMCV IRES with and without the utrophin 3'UTR(A). Bar graphs showing the ratio of expression from the two cistrons, under the control of the 7 different construct (B and C).
Figure 11:
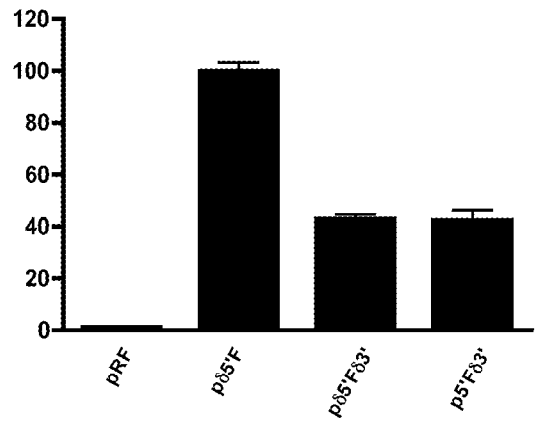
Figure 11:
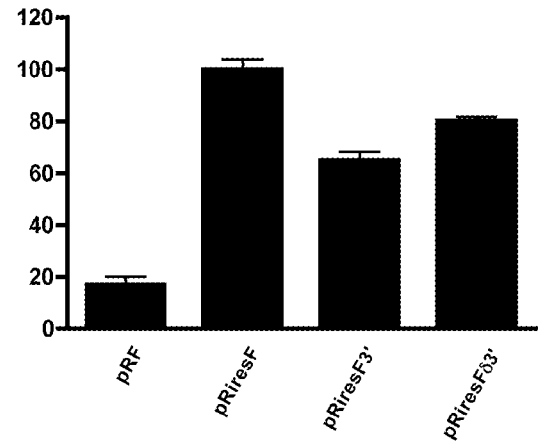

Ribosomal profiling of utrophin-A mRNA in C2C12 muscle cell line by a sucrose gradient provided that utrophin-A is translated inefficiently (FIG. 1). This observation led to an experiment wherein the 5' and 3' UTRs were dissected in order to confirm that utrophin-A non-coding regions are responsible for the translation repression observed. An experiment wherein the 5' or the 3' UTR was cloned into a reporter gene construct (luciferase) showed that these non-coding regions are indeed responsible for this inefficient utrophin-A translation (FIGS. 2 and 10).

Example 2

MicroRNA Candidates

Figure 5:
FIG. 5 is a schematic representation of utrophin 3' UTR microRNA binding sites.

MicroRNA candidates were predicted to target utrophin RNA using the miRanda v1.0.b algorithm. The expression of the predicted microRNAs was confirmed in C2C12 cells or TA by Taqman microRNA assay (FIG. 5).

Example 3

Utrophin-A Repression by MicroRNA

Figure 4:
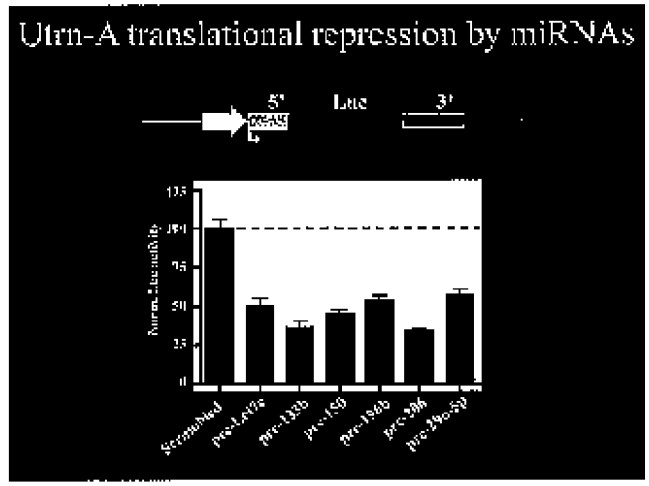
FIG. 4 is a graph showing a decrease in light produced (due to luciferase) on addition of different microRNAs.
Figure 12:
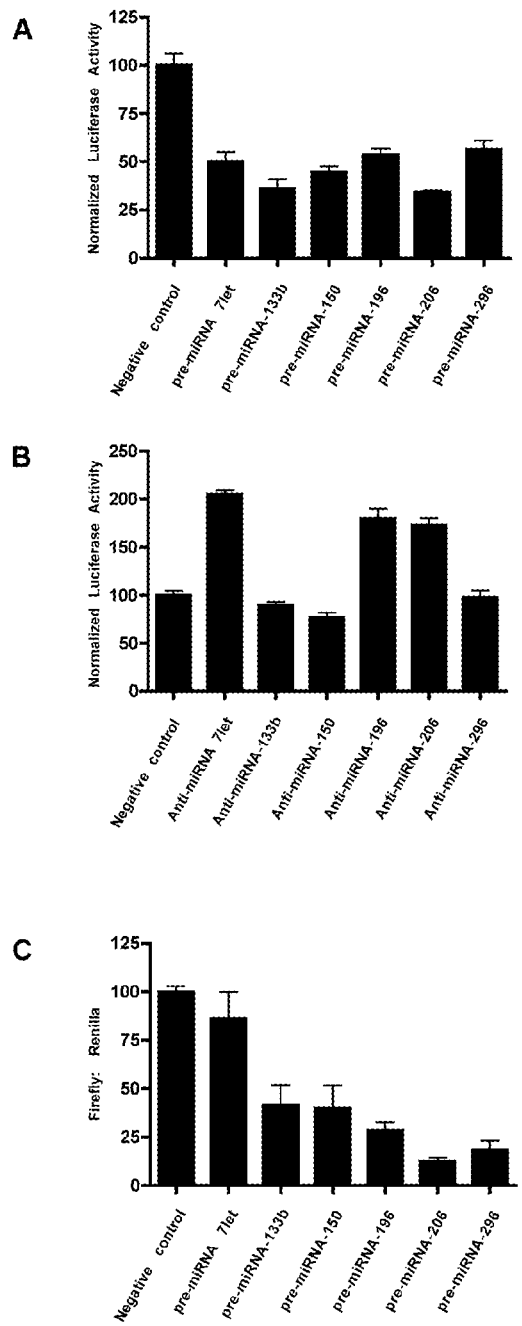
FIG. 12 is a graph showing a decrease in light produced (due to utrophin UTR-luciferase constructs) (A) and firefly (due to utrophin UTR-firefly constructs) expression (C) on addition of different microRNAs. (B) A graph showing an increase in light produced (due to luciferase) on inhibition of certain microRNAs.
Figure 13:
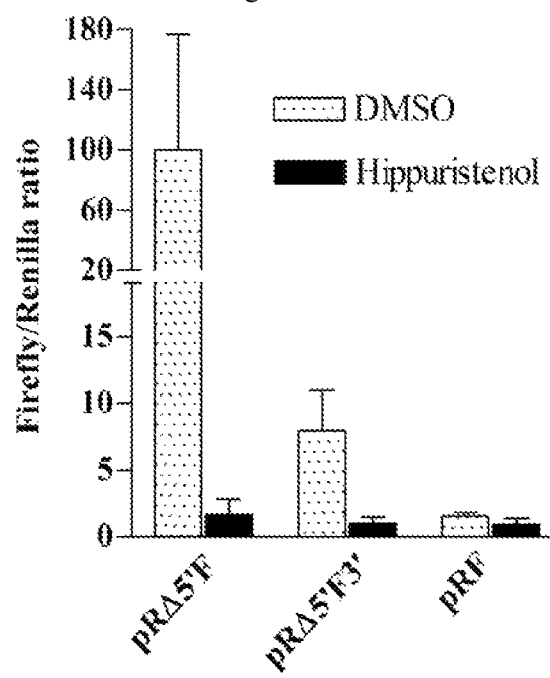
FIG. 13 shows that Utrophin-A IRES requires eIF4A. 3 bicistronic constructs comprising control, or utrophin-A IRES with and without the utrophin 3' UTR. The bar graph shows the firefly/Renilla ratio in cells transfected with plasmids comprising the constructs provided in FIG. 9 with and without the eIF4A inhibitor hippuristanol.
Figure 14:
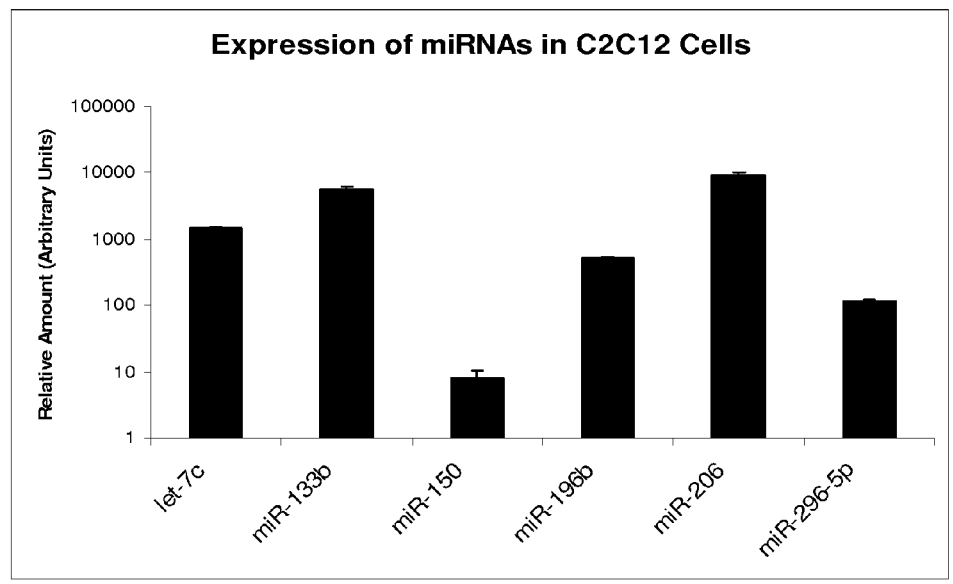
FIG. 14 shows detection and relative quantification of microRNAs in C2C12 muscle cells by miRNA TaqMan assays.
Figure 15:
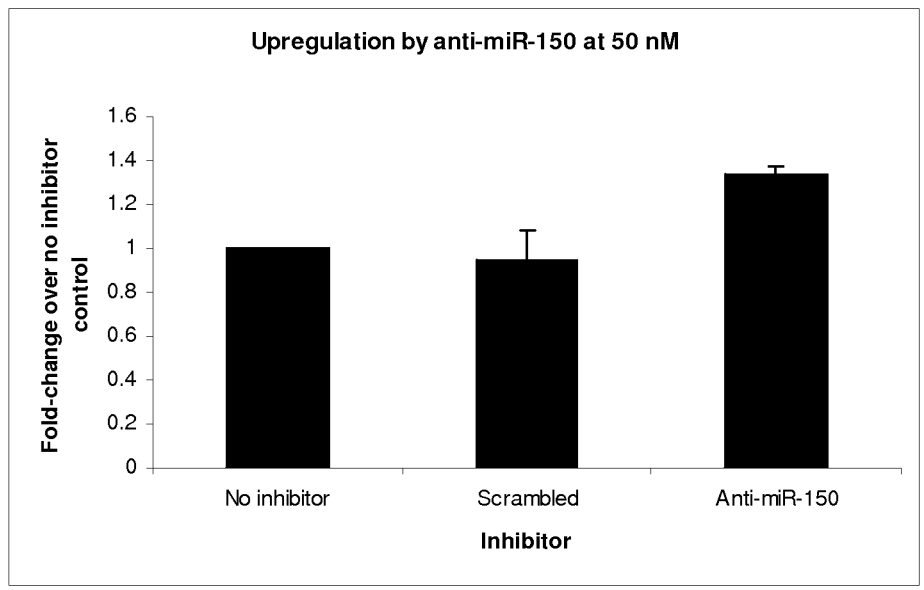
FIG. 15 shows upregulation of 5' Luc3' construct on treatment of miR-150 inhibitor at a lower concentration (50 nM).

C2C12 cells were transfected with a plasmid comprising a construct containing the 5' UTR of the utrophin-A mRNA, a luciferase reporting gene, and the 3' UTR of the utrophin mRNA as described in Example 1. The transfected cells were treated with pre-Let-7c, pre-miR-133b, pre-miR-150, pre-miR-196b, pre-miR-206, pre-miR-296-5p, or a scrambled control sequence. As shown in FIGS. 4 and 12 the scrambled control sequence did not affect luciferase translation, still all 6 microRNA constructs repressed luciferase translation. Thus, Let-7c, miR-133b, miR-150, miR-196b, miR-206, and miR-296-5p are able to repress the translation of a gene comprising the 5' UTR of the utrophin-A mRNA and the 3' UTR of the utrophin mRNA. This experiment demonstrated that Let-7c, miR-133b, miR-150, miR-196b, miR-206, and miR-296-5p are responsible for the repression of utrophin-A mRNA translation. Thus, both 5' and 3' UTRs play an important role in utrophin-A translational repression and the 3' UTR preferentially represses IRES-mediated translation. Moreover, this experiment demonstrates that the 5' UTR of the utrophin-A mRNA and the 3' UTR of the utrophin mRNA are required for the microRNA induced repression.

Example 4

Utrophin is Upregulated by MicroRNA Repression

Figure 6:
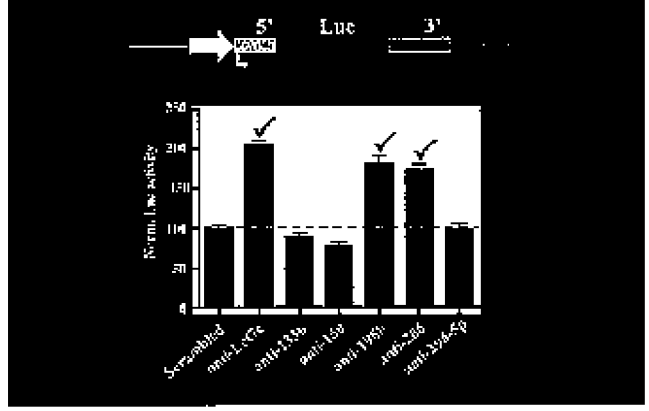
FIG. 6 is a graph showing an increase in light produced (due to luciferase) on inhibition of certain microRNAs.
Figure 7:
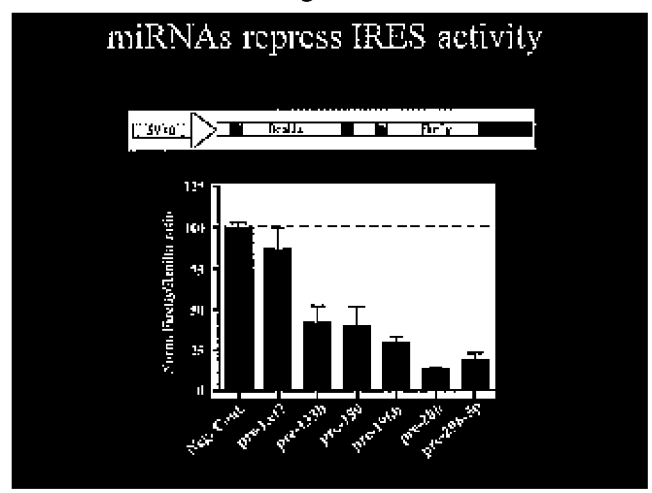
FIG. 7 is a graph showing the IRES repression activity by microRNA molecules that bind utrophin 3' UTR on a reporter gene comprising the utrophin 3' UTR.
Figure 8:
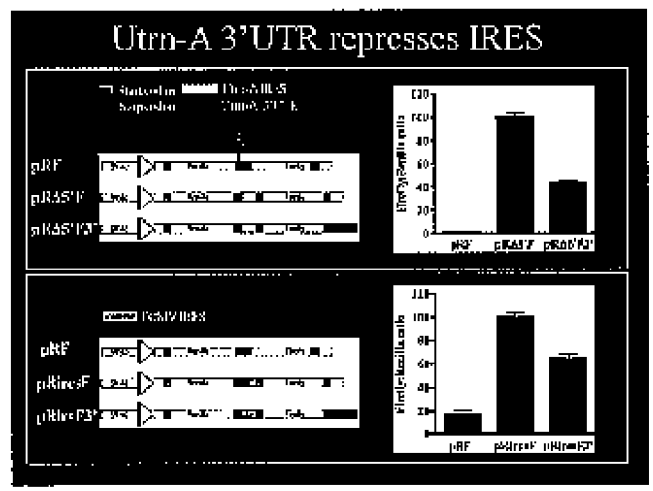
FIG. 8 shows that Utrophin 3' UTR represses IRES. 5 bicistronic constructs comprising control, or utrophin-A or EMCV IRES with and without the utrophin 3'UTR. 2 bar graphs showing ratio of expression of the two cistrons for each construct.
Figure 9:
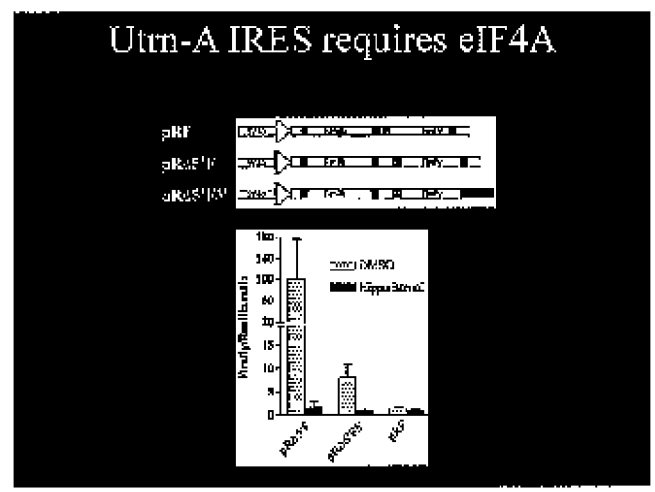
FIG. 9 shows that Utrophin-A IRES requires eIF4A. 3 bicistronic constructs comprising control, or utrophin-A IRES with and without the utrophin 3'UTR. (B) A bar graph showing ratio of expression of the two cistrons for each construct with and without the eIF4A inhibitor hippuristanol.

C2C12 cells were transfected with a plasmid comprising a construct containing the 5' UTR of the utrophin-A mRNA, a luciferase reporting gene, and the 3' UTR of the utrophin mRNA as described in Examples 1 and 3. The transfected cells were treated with antisense sequences: anti-Let-7c, anti-miR-133b, anti-miR-150, anti-miR-196b, anti-miR-206, anti-miR-296-5p, or a scrambled control sequence. The results shown in FIGS. 6 and 12 demonstrate that the scrambled control sequence did not affect luciferase translation; still anti-Let-7c, anti-miR-196b, anti-miR-206, induced luciferase translation. Thus, neutralizing Let-7c, miR-196b, or miR-206 induce the translation of a gene comprising the 5' UTR of the utrophin-A mRNA and the 3' UTR of the utrophin mRNA. This experiment demonstrates that utrophin-A can be induced (upregulated) by at least 2 folds by neutralizing Let-7c, miR-196b, or miR-206 that act as repressors on the UTR segments of the utrophin mRNA. This experiment also provides that this upregulating sequence specific as specific microRNAs did not upregulate utrophin expression including miR-150, miR-133b and miR-296-5p.

The sequence of the negative control inhibitor is: AAGUG-GAUAUUGUUGCCAUCA (SEQ ID NO: 20) and the sequences of the scrambled pre-miRNA are: sense: AGUACUGCUUACGAUACGGtt (SEQ ID NO: 21), and antisense: CCGUAUCGUAAGCAGUACUtt (SEQ ID NO: 22).

Utrophin has two isoforms, A and B. They have different 5' UTRs but the 3' UTRs are the same. Therefore, any mechanism targeting the 3' UTR would be effective for upregulation of either isoform. Utrophin-A and utrophin-B are very similar and either should be effective as a therapy. Accordingly, the results demonstrate the upregulation of both Utrophin-A and utrophin-B isoforms.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method for treating Duchenne Muscular Dystrophy (DMD disease in a subject, comprising the step of administering to said subject a composition for inhibiting utrophin microRNA molecule, wherein said composition comprises a let-7c antisense molecule comprising the nucleic acid sequence set forth in SEQ ID NO: 2, thereby treating said DMD disease in said subject.

* * * * *